(12) United States Patent
Bhushan et al.

(10) Patent No.: US 8,961,934 B2
(45) Date of Patent: Feb. 24, 2015

(54) FIBROSIS SPECIFIC MULTIMERIC PEPTIDOMIMETIC RADIOTRACERS

(76) Inventors: Kumar Ranjan Bhushan, St Louis, MO (US); Preeti Misra, St Louis, MO (US)

( * ) Notice: Subject to any disclaimer, the term of this patent is extended or adjusted under 35 U.S.C. 154(b) by 59 days.

(21) Appl. No.: 13/590,189

(22) Filed: Aug. 21, 2012

(65) Prior Publication Data
US 2014/0058071 A1    Feb. 27, 2014

(51) Int. Cl.
*A61K 49/00* (2006.01)
*A61K 51/04* (2006.01)
*A61K 49/10* (2006.01)

(52) U.S. Cl.
CPC ............ *A61K 51/0482* (2013.01); *A61K 49/106* (2013.01)
USPC .......................................................... 424/9.1

(58) Field of Classification Search
USPC .......................................................... 424/9.1
See application file for complete search history.

(56) References Cited

U.S. PATENT DOCUMENTS

2012/0244074 A1* 9/2012 Solbakken .................... 424/1.89

* cited by examiner

*Primary Examiner* — Michael G Hartley
*Assistant Examiner* — Melissa Perreira (57) ABSTRACT

The present invention describes peptidomimetic radiotracers. In particular, the present invention discloses fibrosis specific multimeric small-molecule peptidomimetic radiotracers.

14 Claims, 8 Drawing Sheets

FIBROSIS SPECIFIC MULTIMERIC PEPTIDOMIMETIC RADIOTRACERS

FIELD OF THE INVENTION

The present invention discloses fibrosis specific multimeric small-molecule peptidomimetic radiotracers.

BACKGROUND

Nuclear medicine, which uses radioactive chemical elements called radionuclides to diagnose or treat diseases, has grown tremendously over the past 50 years. Nuclear medicine encompasses a variety of imaging devices and therapeutics that use radionuclides. Nuclear imaging devices, such as positron emission tomography (PET) and single photon emission computed tomography (SPECT) scans, work by tracking radioactive chemicals that are swallowed, inhaled, or injected into the body, where they accumulate in the organ or tissue of interest and reveal biochemical changes. Such imaging devices enable physicians to diagnose diseases including cancer, cardiovascular disease, and neurological disorders (e.g., Alzheimer's and Parkinson's diseases) in their initial stages. These techniques allow doctors to obtain medical information that would otherwise require more costly and invasive procedures like surgery or biopsy. Nuclear imaging devices are also valuable for conducting research on the biology of human diseases and for developing and testing new treatment approaches.

Although nuclear medicine has already made enormous contributions to biomedical research and disease management, its promise is only beginning to be realized in such areas as drug development, preventive health care, and personalized medicine. However, there remain two major problems in the field of nuclear medicine and imaging: 1) the complex and expensive chemistry infrastructure required for traditional radiolabeling or radionuclide production, and 2) the difficulty in producing high affinity targeted-(radio) ligands specific for particular disease.

Quantitative imaging of liver fibrosis or fibrogenesis has been elusive. Integrin $\alpha_v\beta_6$ mediates attachment of activated epithelia to fibronectin, vitronectin, and tenascin {Breuss, 1995; Midwood, 2006} and activates profibrogenic cytokine TGFβ {Munger, 1999} implying its instrumental role in driving fibrogenesis. Integrin receptors frequently recognize a core amino acid sequence, Arg-Gly-Asp (RGD), in their target ligands. Therefore, inhibitors with the RGD sequence can inhibit one or a small subset of such RGD-dependent integrins, and are invaluable in defining their biological functions. However, peptidic inhibitors have several disadvantages as low molecular weight inhibitors, including their instability to serum degradation (which can be circumvented by use of small cyclic peptides {Kessler, 1982}, and poor pharmacokinetics. Nevertheless, non-RGD peptides have been discovered with high specificity and inhibitory activity for $\alpha_v\beta_6$ {Kloczewiak, 1984; Kraft, 1999}, and, as of yet, non-peptidic inhibitor of $\alpha_v\beta_6$ are not known for use in nuclear imaging of $\alpha_v\beta_6$ in liver fibrosis.

SUMMARY

Nuclear medicine is a highly multi-disciplinary specialty that develops and uses instrumentation and radiopharmaceuticals to study physiological processes and non-invasively diagnose, stage, and treat diseases. A radiopharmaceutical is either a radionuclide alone, such as iodine-131 or a targeted one, radionuclide that is attached to a carrier molecule (a drug, protein, or peptide) or particle, which when introduced into the body by injection, swallowing, or inhalation, accumulates in the organ or tissue of interest. In a nuclear medicine scan, a radiopharmaceutical is administered to the patient, and an imaging instrument, such as PET and SPECT, detects radiation is used to show biochemical changes in the body. Nuclear medicine imaging in contrast to other imaging techniques that mainly show anatomy (e.g., conventional ultrasound, computed tomography [CT], or magnetic resonance imaging [MRI]), can provide important quantitative functional information about normal tissues or disease conditions in living subjects. For treatment, highly targeted radiopharmaceuticals may be used to deposit lethal radiation at tumor sites.

PET is a noninvasive nuclear medicine imaging technique that exploits the unique decay physics of positron-emitting radionuclides and produces a three-dimensional image of radionuclide distribution. SPECT is an another common non-invasive nuclear medicine imaging technique in which gamma-ray emissions from a radioisotope are used to localize radiotracer distribution. PET and SPECT each have distinct advantages and disadvantages that make them useful for detecting certain conditions. Each technique uses different properties of radioactive elements in creating an image. For example, one of the advantages of SPECT compared with PET is that more than one radiotracer can be used at a time. In addition, the longer half-life of radionuclides used with SPECT makes this imaging procedure more readily available to the medical community at large. However, PET images have higher sensitivity than SPECT images by a factor of 2 to 3 and use radiopharmaceuticals that provide more physiological information.

SPECT/CT and PET/CT are routinely used in research and clinics. The addition of CT to these scanners permits attenuation correction and provides anatomical landmarks. A new generation of time-of flight (TOF) PET scanners {Conti, 2005; Surti, 2006} offers a 2-fold improvement in resolution or sensitivity (but not both) and is especially useful for scanning large patients. An even newer advancement is the fusion of PET or SPECT with MRI. Although it is unclear how well these scanners will perform with respect to attenuation correction, their anatomical imaging is outstanding.

Although radionuclides are used for PET and SPECT scanners, there is a need for new targeted radionuclides. Non-targeted and non-specific radionuclides have several disadvantages. For example, the term "PET scanning" generally is synonymous with the use of 2-[$^{18}$F]fluoro-2-deoxy-D-glucose ($^{18}$FDG) as the radiotracer. Although valuable as a cancer biomarker, $^{18}$FDG has variable uptake and retention in many tumors {kelloff, 2005}, as well as high uptake in normal tissues and organs [kumar, 2006]. Targeted RGD conjugated radionuclides are frequently used in recent years for integrins, particularly for the $\alpha_v\beta_3$ expression. However, there is no known nuclear imaging agent specifically for $\alpha_v\beta_6$-integrin in liver fibrosis.

Nature often takes advantage of multimerization to decrease ligand off-rate and improve affinity of cell surface binders {Kitov, 2003; Mammen, 1998}. There is a general need to find suitable scaffolds for the assembly of multiple targeting ligands and contrast agents in hope that multimerization would improve the performance of cancer specific ligands.

Several different multivalent scaffolds have been used successfully in past particularly for applications in carbohydrate/lectin interactions {Lindhorst, 2002; Lundquist, 2002} but also for peptide/protein interactions {Wright, 2001} and in context of tumor targeting {Carlson, 2007; Thumshirn, 2003}. Among these scaffolds are small molecules with few conjugation sites (~2-10) and larger systems like dendrimers {Voegtle, 2007} and polymers {Haag, 2006}.

Activated hepatic stellate cells and myofibroblasts HSC/MF play a central role in the development of chronic liver diseases {Friedman, 2008}. They deposit an excess of extracellular matrix components, which leads to fibrosis and finally cirrhosis. Cirrhosis is defined as architectural distortion of the liver with severe vascular and functional abnormalities {Schuppan, 2008}. Certain cell-cell and especially cell-matrix receptors, mainly integrins, are markedly upregulated on activated endothelia and HSC/MF, transmitting migratory, growth promoting, and other profibrogenic signals. Treatment of fibrotic liver diseases and cirrhosis with specific $\alpha_v\beta_6$-integrin antagonists can block endothelial, HSC/MF and epithelial cell migration and activation, and thus mitigate or even reverse fibrogenesis. Analogous to the liver, activated myofibroblast-like and epithelial cells are central in the pathogenesis of other progressive fibrotic diseases. Specific $\alpha_v\beta_6$-integrin antagonists can also be used to treat fibrotic disorders of other organs, e.g., the pancreas, intestine, lungs, heart, kidneys, arteries, or skin.

Integrin $\alpha_v\beta_6$ is a fibronectin/tenascin receptor that is also involved in cell surface TGFβ activation. Its expression is highly restricted and found only on some activated epithelia during proliferation, inflammation and fibrogenesis. $\alpha_v\beta_6$ is expressed de novo on activated cholangiocytes in rodent and human liver fibrosis and its levels correlate with fibrosis progression regardless of the underlying liver disease. Integrins are a family of heterodimeric cell surface receptors that frequently recognize a core amino acid sequence, RGD, in their target ligands. Therefore, inhibitors with the RGD sequence can inhibit one or a small subset of such RGD-dependent integrins, and are invaluable in defining their biological functions. Quantitative imaging of liver fibrosis or fibrogenesis has been elusive. Recently, non-RGD peptides have been discovered with high specificity and inhibitory activity for $\alpha_v\beta_6$ {Kloczewiak, 1984; Kraft, 1999}, however, as of yet, non-peptidic inhibitor of $\alpha_v\beta_6$ are not known for use in nuclear imaging of $\alpha_v\beta_6$ in liver fibrosis. Therefore, high affinity $\alpha_v\beta_6$-specific peptidomimetics are attractive candidates for hepatic fibrogenesis imaging because of the correlation of selective upregulation of $\alpha_v\beta_6$-integrin during fibrosis progression.

The present invention describes a development of multimeric $\alpha_v\beta_6$-integrin specific radiotracers. A non-peptidic inhibitor (3-(S)-3-benzyloxy-2-(5-(pyridin-2-ylamino)pentanoyl-amino)propionylamino)-3-(3,5-dichlorophenyl)propionic acid [BDP acid] {Popov, 2008} is multimerized for high affinity on $\alpha_v\beta_6$-integrin. The multimeric $\alpha_v\beta_6$-integrin specific radiotracers could theoretically bind multivalently and thus more avidly to target cell.

Figure 1:
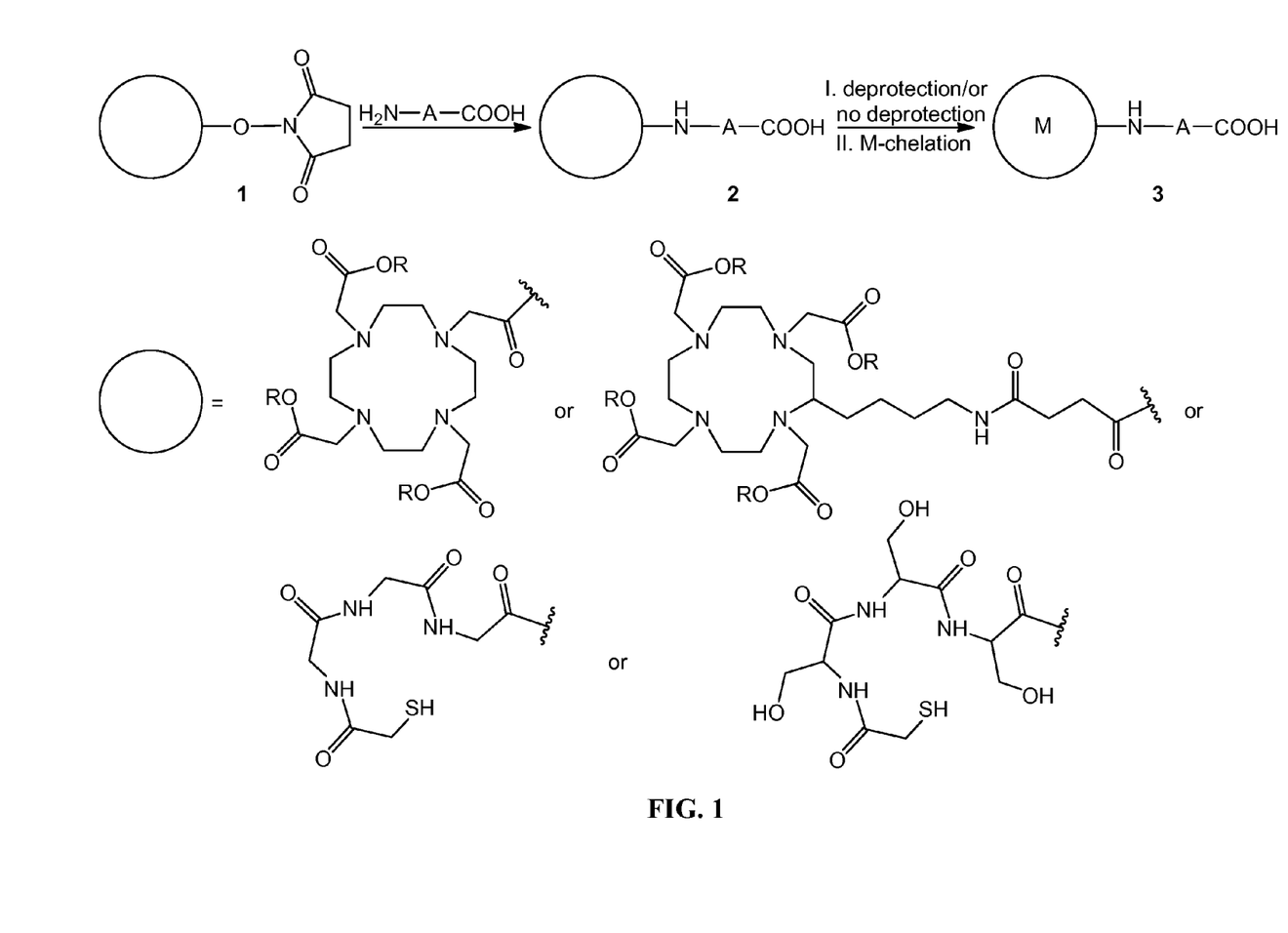
FIG. 1 represents a metal chelate conjugated to a linking moiety having carboxylic moiety at one end.

In one aspect of present invention, an organic chelating ligand is reacted with a linking moiety, having a primary amine and a carboxylic moiety at opposing ends, followed by deprotection of one or more carboxylic acid ester of an organic chelating ligand to yield one or more carboxylic acid functionality. Chelation of a metal ion at an organic chelating ligand results in a metal chelate (FIG. 1). In such aspect, linker, $H_2N$-A-COOH is an amino acid or A is independently selected from an alkane, polyethylene glycol and polypropylene glycol. M is independently selected from Cu, Fe, Mn, Re, In, Tb, Tm, Tl, Sm, Lu, Ga, Yb, Y, Gd, Eu, and a lanthanide. R is t-butyl ester, ester or hydrogen. In one embodiment, amino acid is natural amino acid. In some embodiment, amino acid is unnatural amino acid. In some embodiments, an alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, deprotection step is not required. In some embodiments, Cu, Fe, Mn, Tm, Yb, Y, Gd, Eu, or a lanthanide is chelated for MRI. In some embodiments, Cu, Tc, Re, In, Tb, Tm, Tl, Sm, Lu, Ga, or Y is chelated for nuclear imaging.

Figure 2:
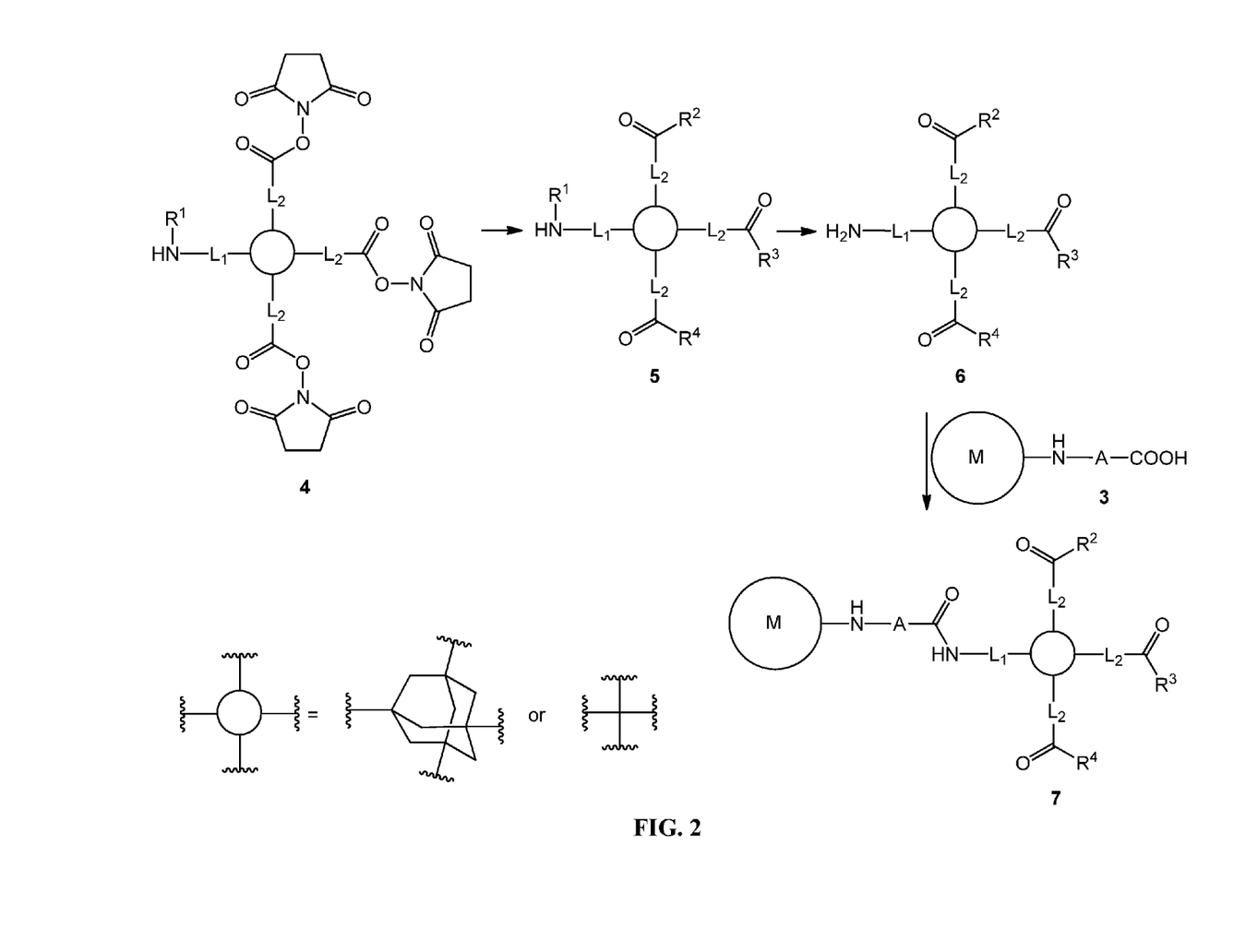
FIG. 2 represents a multimeric peptidomimetic radiotracer with a linking moiety in which metal is chelated before reaction of an amine containing targeting ligand conjugated multivalent scaffold.

In an another aspect of present invention, a targeting ligand is conjugated with multivalent scaffold followed by deprotection of amino protecting group to generate an amine containing targeting ligand conjugated multivalent scaffold. Reaction of an amine containing targeting ligand conjugated multivalent scaffold with carboxylic moiety of metal chelate to results in multimeric peptidomimetic radiotracer (FIG. 2). In such aspect, $R^1$ is independently selected from Boc, Fmoc, Ac, Cbz, Bz and Bn. $R^2$, $R^3$ and $R^4$ are OH or $L_1$, $L_2$ and $L_3$ are linkers independently selected from alkane, amino acid, —NHCO(CH$_2$)$_5$—, polyethylene glycol and polypropylene glycol. In one embodiment, amino acid is natural amino acid. In some embodiments, amino acid is unnatural amino acid. In some embodiments, an alkane is C0-C20 straight chain carbon unit. In some embodiments, polyethylene glycol is 1 to 20 ethylene glycol unit. In some embodiments, polypropylene glycol is 1 to 20 propylene glycol unit.

The present invention describes peptidomimetic radiotracers. Particularly, the present invention discloses fibrosis specific multimeric small-molecule peptidomimetic radiotracers. Specifically, trimeric small-molecule peptidomimetic radiotracer have significantly higher in vitro $\alpha_v\beta_6$-binding affinity over monomeric small-molecule peptidomimetic radiotracer.

DETAILED DESCRIPTION

In a present invention, synthetic strategy is developed for multimeric peptidomimetic radiotracers for targeted fibrosis imaging. Metal chelate is obtained with or without linker moiety and deprotection. A targeting ligand is conjugated with multivalent scaffold and following couple of steps generating an amine containing targeting ligand conjugated multivalent scaffold which is reacted with carboxylic moiety of metal chelate to results in multimeric peptidomimetic radiotracers.

The multimeric peptidomimetic radiotracers of present invention are prepared according to the methods known in the art, as illustrated in FIGS. 1-6 and described for specific compounds in examples 1-4. Products are characterized by analytical HPLC, NMR and LCMS.

Figure 4:
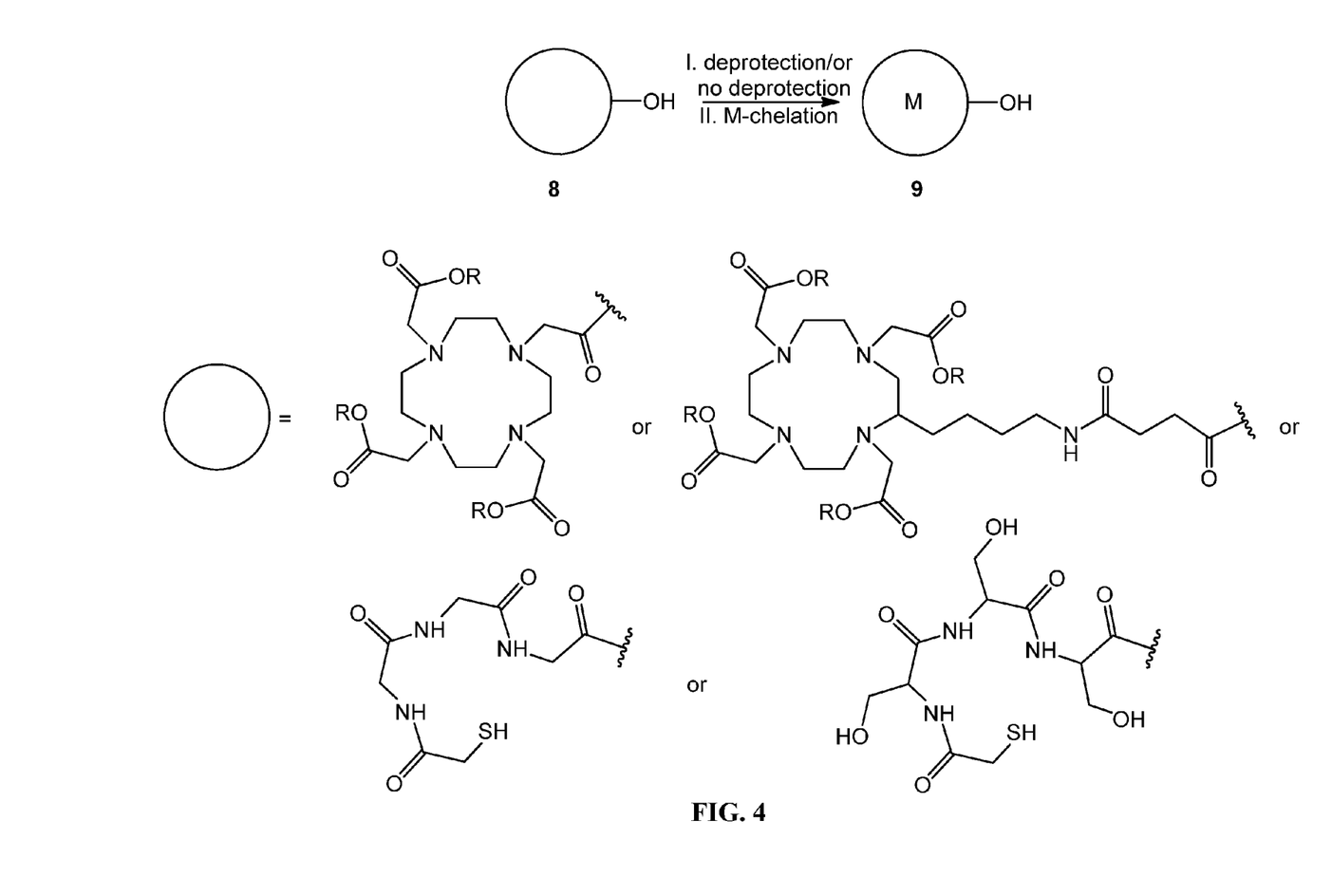
FIG. 4 represents a metal chelate having carboxylic moiety at one end.

FIG. 1 and FIG. 4 of present invention describe synthetic schemes for metal chelates with carboxylic terminal moiety. Metal chelates with carboxylic terminal moiety are obtained with or without linker moiety and deprotection.

Figure 5:
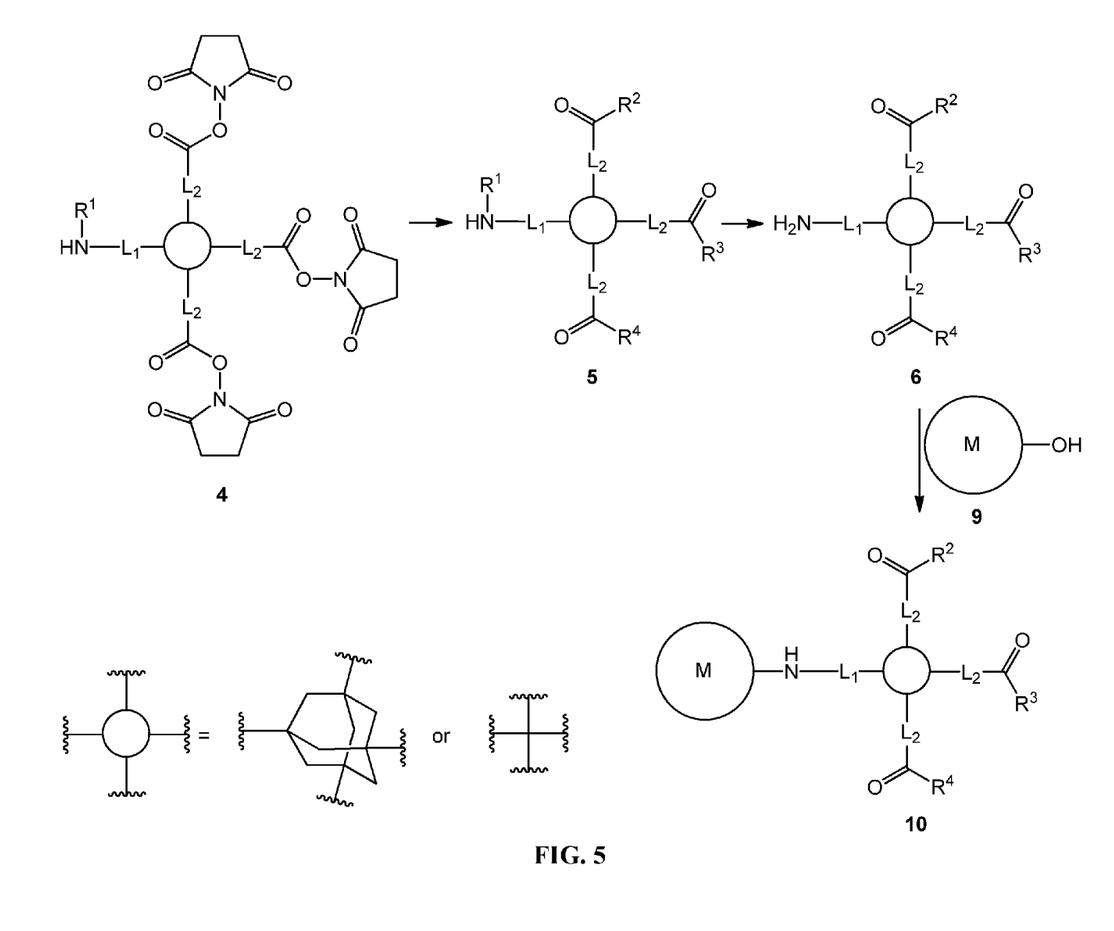
FIG. 5 represents a multimeric peptidomimetic radiotracer in which metal is chelated before reaction of an amine containing targeting ligand conjugated multivalent scaffold.

FIG. 2 and FIG. 5 of present invention describe synthetic schemes for multimeric peptidomimetic radiotracer with or without a linking moiety in which metal is chelated before reaction of an amine containing targeting ligand conjugated multivalent scaffold.

Figure 3:
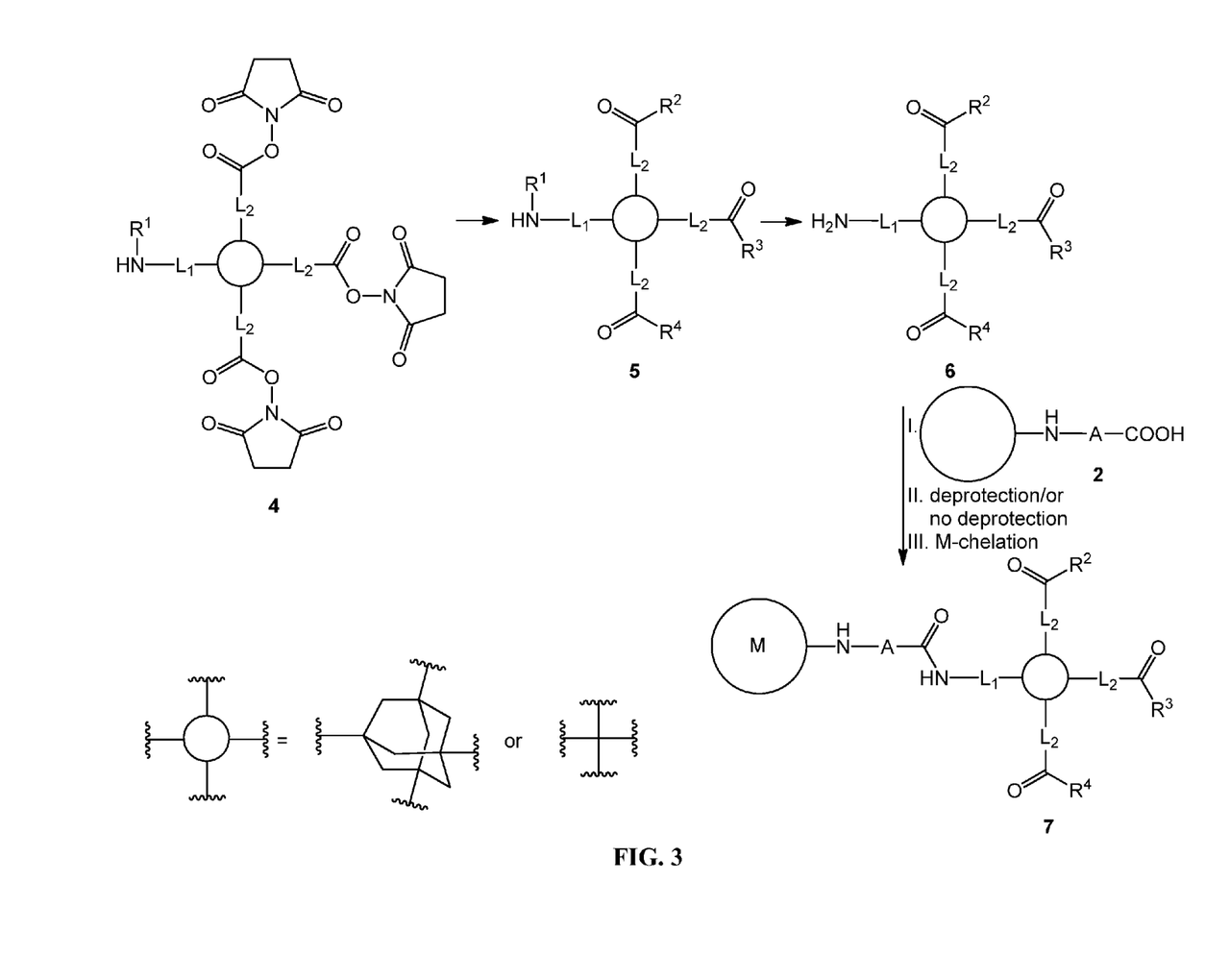
FIG. 3 represents a multimeric peptidomimetic radiotracer with a linking moiety in which metal is chelated after reaction of an amine containing targeting ligand conjugated multivalent scaffold.
Figure 6:
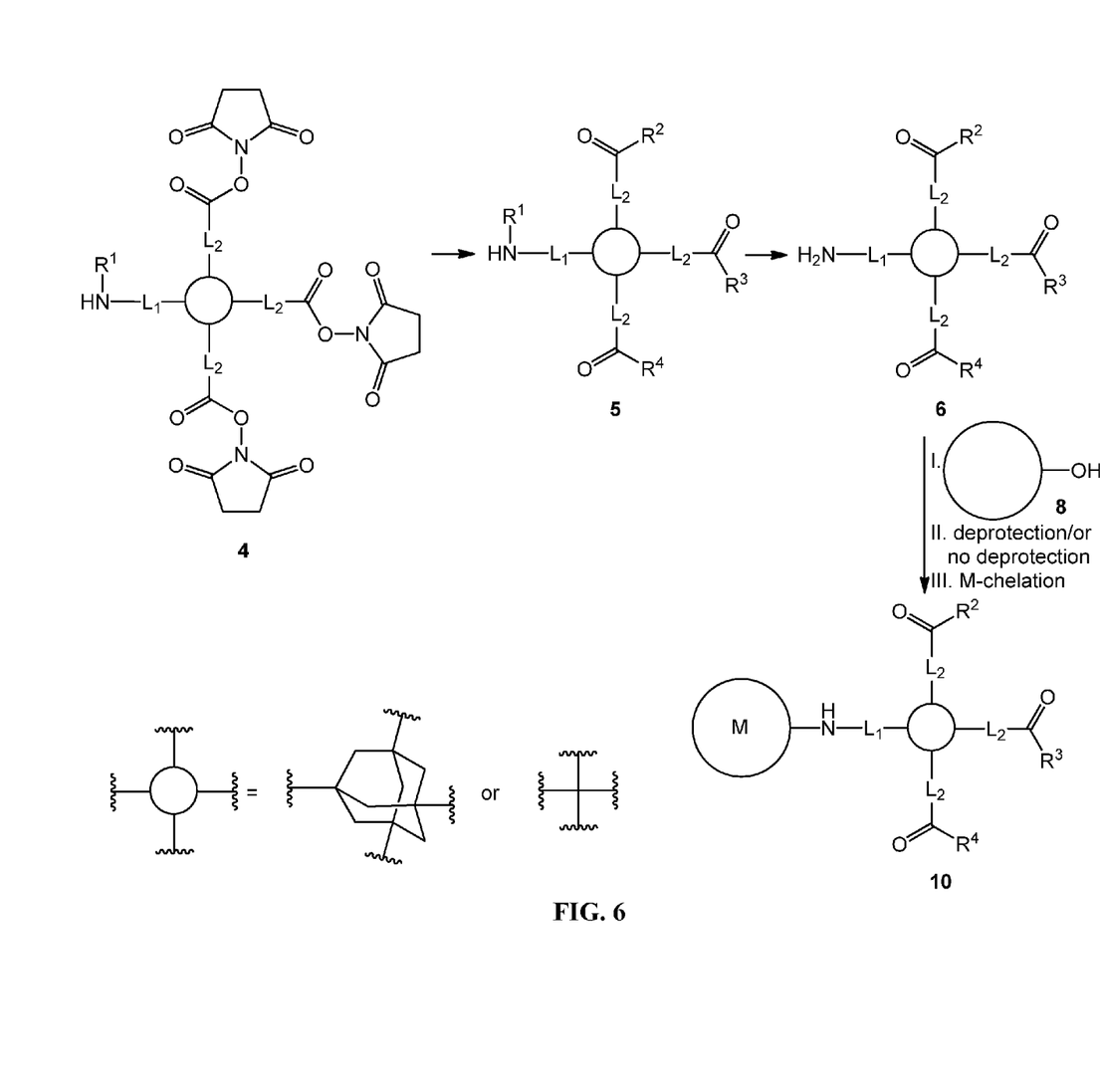
FIG. 6 represents a multimeric peptidomimetic radiotracer in which metal is chelated after reaction of an amine containing targeting ligand conjugated multivalent scaffold.

FIG. 3 and FIG. 6 of present invention describe synthetic schemes for multimeric peptidomimetic radiotracer with or without a linking moiety in which metal is chelated after reaction of an amine containing targeting ligand conjugated multivalent scaffold.

In one aspect, the present invention provides a contrast agent having a formula selected from the group of:

In such aspect,

R is

$L_1$, $L_2$ and $L_3$ are linkers, is a metal chelate independently selected from:

In one embodiment, linkers are independently selected from alkane, amino acid, —NHCO(CH$_2$)$_5$—, polyethylene glycol and polypropylene glycol. In some embodiments, amino acid is natural amino acid. In some embodiments, amino acid is unnatural amino acid. In some embodiments, an alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, M is independently selected from Cu, Fe, Mn, Re, In, Tb, Tm, Tl, Sm, Lu, Ga, Yb, Y, Gd, Eu, and a lanthanide. In some embodiments, Cu, Fe, Mn, Tm, Yb, Y, Gd, Eu, or a lanthanide is chelated for MRI. In some embodiments, Cu, Tc, Re, In, Tb, Tm, Tl, Sm, Lu, Ga, or Y is chelated for nuclear imaging.

In an another aspect, the present invention provides a method of making a contrast agent. The method involve steps of:

(a) Starting synthesis with an organic chelating ligand selected from the group of:

where, R is t-butyl ester, ester or hydrogen, and
R$^1$ is

(b) reacting an organic chelating ligand with a linking moiety having a primary amine and a carboxylic moiety at opposing ends, (c) deprotecting one or more carboxylic acid ester of an organic chelating ligand to yield one or more carboxylic acid functionality, (d) chelating a metal ion to result in a metal chelate, where a linking moiety on a metal chelate having a carboxylic moiety, (e) providing a multivalent scaffold selected from the group of:

-continued where, $R^2$ is Boc, Fmoc, Ac, Cbz, Bz or Bn,
$L_1$ and $L_2$ are linkers,
and
$R^1$ is (f) conjugating a multivalent scaffold with a targeting ligand to yield one or more targeting ligand conjugated multivalent scaffold, (g) deprotecting an amino protecting group on one or more targeting ligand conjugated multivalent scaffold to obtain an amine containing targeting ligand conjugated multivalent scaffold, and (h) reacting an amine containing targeting ligand conjugated multivalent scaffold with a carboxylic moiety of a metal chelate under a condition capable of forming an amide bond to results in a contrast agent.

In one embodiment, linkers are independently selected from alkane, amino acid, —NHCO(CH$_2$)$_5$—, polyethylene glycol and polypropylene glycol. In some embodiments, amino acid is natural amino acid. In some embodiments, amino acid is unnatural amino acid. In some embodiments, an alkane is C0-C20 straight chain carbon unit. In some embodiments, polyethylene glycol is 1 to 20 ethylene glycol unit. In some embodiments, polypropylene glycol is 1 to 20 propylene glycol unit. A targeting ligand is where, $L_3$ is independently selected from the group of alkane, amino acid, polyethylene glycol and polypropylene glycol. In some embodiments, metal ion is independently selected from Cu, Fe, Mn, Re, In, Tb, Tm, Tl, Sm, Lu, Ga, Yb, Y, Gd, Eu, and a lanthanide. In some embodiments, Cu, Fe, Mn, Tm, Yb, Y, Gd, Eu, or a lanthanide is chelated for MRI. In some embodiments, Cu, Tc, Re, In, Tb, Tm, Tl, Sm, Lu, Ga, or Y is chelated for nuclear imaging.

In an another aspect, the present invention provides a method of making a contrast agent. The method involve steps of:

(a) Starting a synthesis with an organic chelating ligand selected from the group of:

where, R is t-butyl ester, ester or hydrogen;
and
$R^1$ is (b) reacting an organic chelating ligand with a linking moiety to yield a terminal carboxylic moiety on an organic chelating ligand, where a linking moiety having a primary amine and a carboxylic moiety at opposing ends, (c) providing a multivalent scaffold selected from the group of:

where, $R^2$ is Boc, Fmoc, Ac, Cbz, Bz or Bn, $L_1$ and $L_2$ are linkers, and $R^1$ is (d) conjugating a multivalent scaffold with a targeting ligand to yield one or more targeting ligand conjugated multivalent scaffold, (e) deprotecting an amino protecting group on one or more targeting ligand conjugated multivalent scaffold to obtain an amine containing targeting ligand conjugated multivalent scaffold, (f) reacting an amine containing targeting ligand conjugated multivalent scaffold with a terminal carboxylic moiety on an organic chelating ligand under a condition capable of forming an amide bond to results in an organic chelating ligand containing targeting ligand conjugated multivalent scaffold, (g) deprotecting one or more carboxylic acid ester of an organic chelating ligand containing targeting ligand conjugated multivalent scaffold to yield one or more carboxylic acid functionality, and (h) chelating a metal ion to one or more carboxylic acid functionality on an organic chelating ligand containing targeting ligand conjugated multivalent scaffold to results in a contrast agent.

In one embodiment, linkers are independently selected from alkane, amino acid, —NHCO(CH$_2$)$_5$—, polyethylene glycol and polypropylene glycol. In some embodiments, amino acid is natural amino acid. In some embodiments, amino acid is unnatural amino acid. In some embodiments, an alkane is C0-C20 straight chain carbon unit. In some embodiments, polyethylene glycol is 1 to 20 ethylene glycol unit. In some embodiments, polypropylene glycol is 1 to 20 propylene glycol unit. A targeting ligand is where, $L_3$ is independently selected from the group of alkane, amino acid, polyethylene glycol and polypropylene glycol. In some embodiments, metal ion is independently selected from Cu, Fe, Mn, Re, In, Tb, Tm, Tl, Sm, Lu, Ga, Yb, Y, Gd, Eu, and a lanthanide. In some embodiments, Cu, Fe, Mn, Tm, Yb, Y, Gd, Eu, or a lanthanide is chelated for MRI. In some embodiments, Cu, Tc, Re, In, Tb, Tm, Tl, Sm, Lu, Ga, or Y is chelated for nuclear imaging.

The multimeric small-molecule peptidomimetic radiotracers generated by present invention can be used for, e.g., PET, SPECT, radioimmuno, and magnetic resonance applications for detection, imaging and treatment of fibrosis and other abnormalities. In particular, multimeric small-molecule peptidomimetic radiotracers generated by present invention are specific for integrin α$_v$β$_6$, a fibronectin/tenascin receptor in fibrosis. Specifically, trimerization of an α$_v$β$_6$-selective small-molecule using a rigid admantane core results in significantly higher in vitro affinity for α$_v$β$_6$ in comparison to the monomeric form of an α$_v$β$_6$-selective small-molecule without a rigid admantane core.

The binding affinities and specificities of Re-derivatives of monomer 15b (FIG. 7) and trimer 18b (FIG. 8) are evaluated for HT-29 and Huh-7 cells. Results of the cell-binding assay are plotted in sigmoid curves for the displacement of corresponding radiotracers, both the test compounds inhibited the binding of $^{99m}$Tc-labeled tracers (integrin α$_v$β$_6$ specific) to HT-29 cells in a concentration dependent manner. The cell binding assay demonstrates that the trimer 18 has about four times higher integrin α$_v$β$_6$ avidity than monomer 15 (attributed to the polyvalency effect) {Mammen, 1998}.

EXAMPLES

Figure 7:
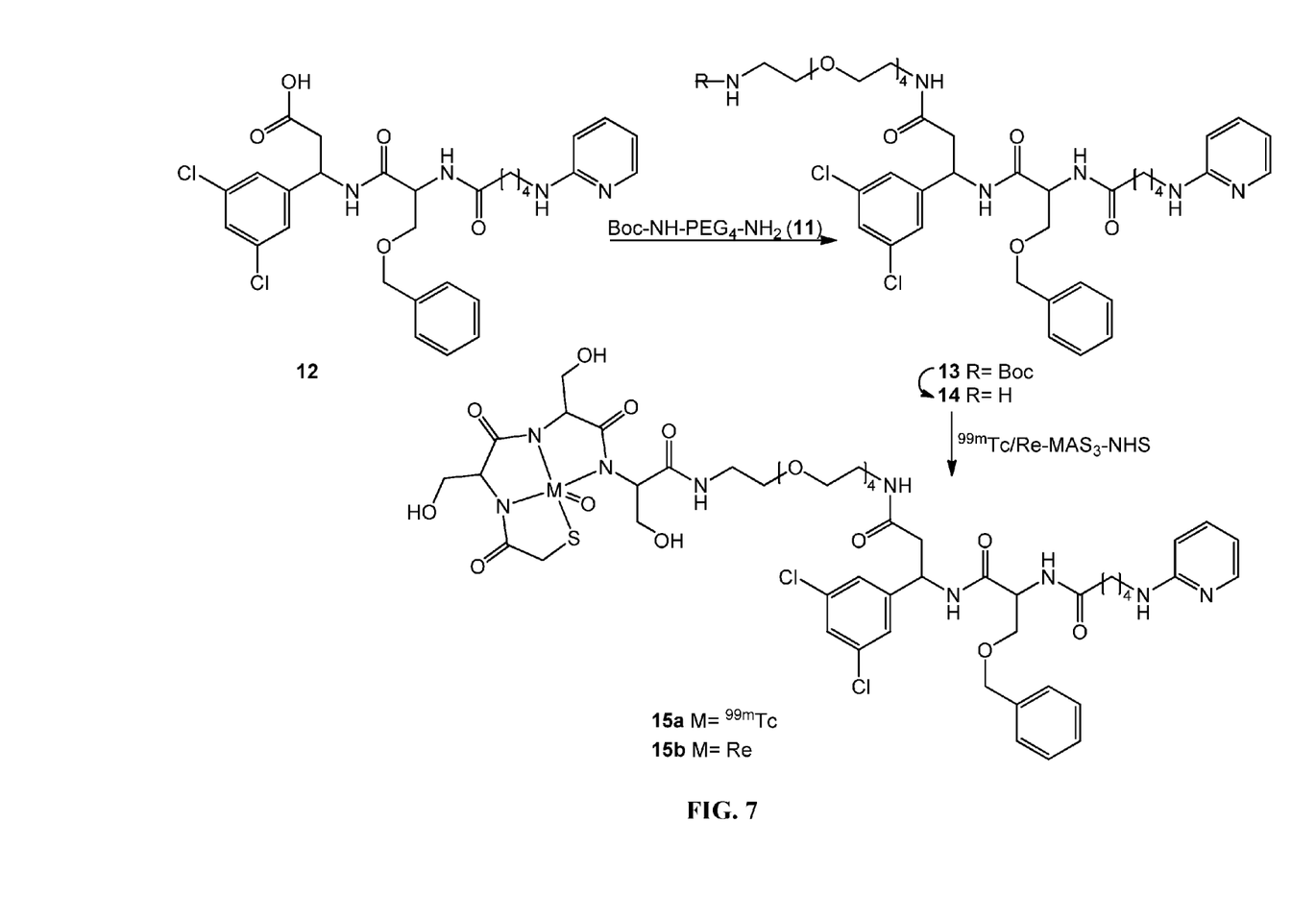
FIG. 7 represents a synthetic scheme for preparation of monomeric form of an $\alpha_v\beta_6$-selective small-molecule radiotracer without a rigid admantane core.

1. Preparation of BDP Acid Conjugated Terminal Amine Monomer (FIG. 7)

TSTU (70 μmol), DIEA (80 μmol) and Boc-NH-PEG$_4$-NH$_2$ (68 μmol) are added to BDP acid 12 (68 μmol) in 1 mL DMF at 0° C. After 10 min, the ice bath is removed and stirring is continued for 2 h at room temperature (RT). The reaction mixture is poured over 3 mL ice cold water and purified by preparative HPLC. After concentration and lyophilization, Boc amine monomer 13 is obtained which is further treated with 1 mL 95% trifluoroacetic acid (TFA), and the solution is stirred at RT for 2.5 h. The excess TFA is removed by N$_2$ stream. After lyophilization, the BDP acid conjugated terminal amine monomer 14 (87%) is obtained without further purification.

Figure 8:
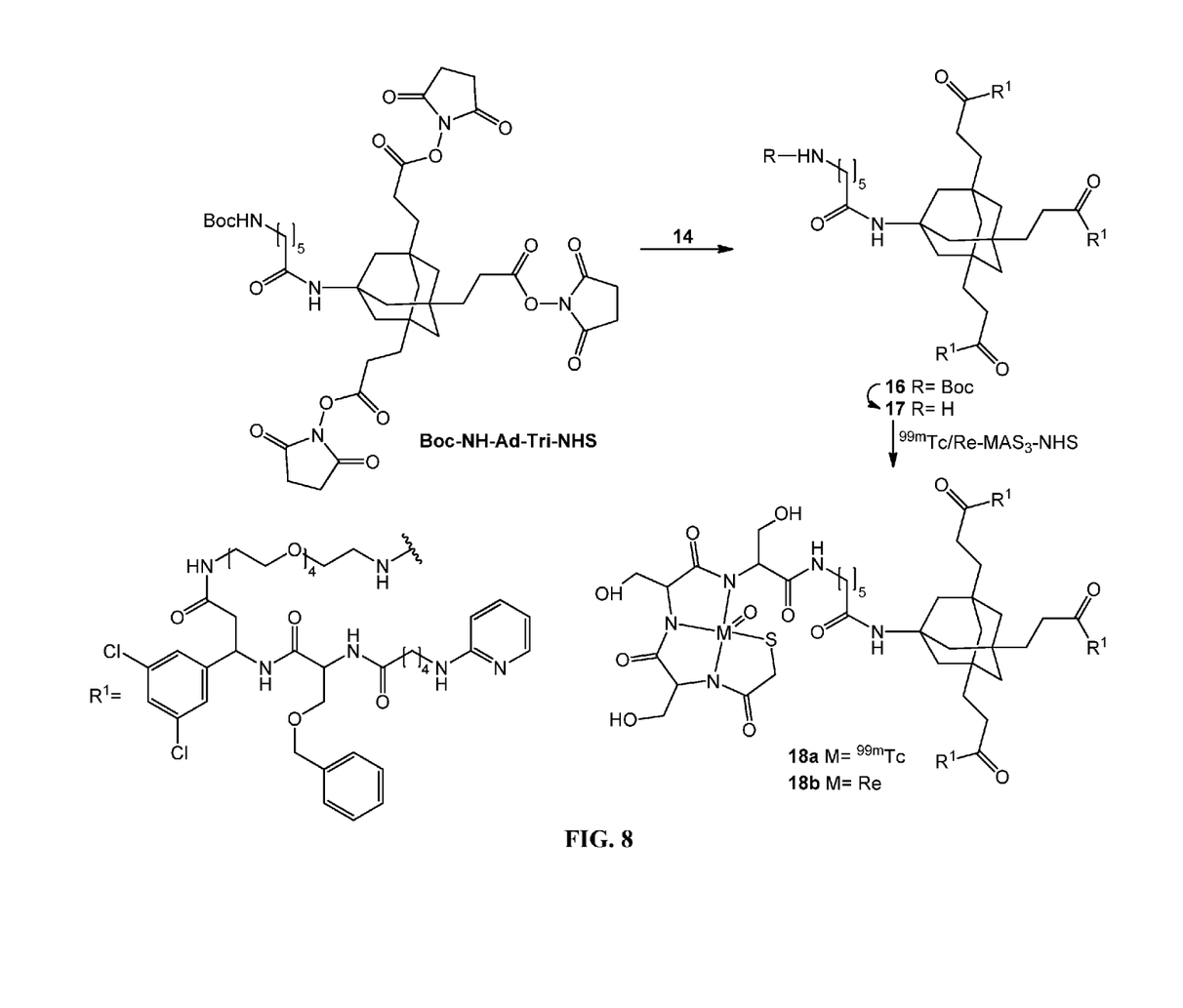
FIG. 8 represents a synthetic scheme for preparation of trimeric form of an $\alpha_v\beta_6$-selective small-molecule radiotracer using a rigid admantane core.

2. Preparation of Adam BDP Acid Conjugated Terminal Amine Trimer (FIG. 8)

BDP acid conjugated terminal amine monomer 14 (60 μmol) is dissolved in 400 μL of DMSO and pure triethylamine (120 µmol). After 5 min, a solution of Boc-NH-Ad-Tri-NHS (15 µmol) {Humblet, 2009} in 200 µL of DMSO is added. The reaction mixture is stirred at RT for 4 h. The compound 16 is purified after dilution into a final volume of 5 mL with ice cold water by preparative HPLC system. After lyophilization, product 16 is treated with 95% TFA (1 mL) for 3 h. Excess TFA is removed under nitrogen and after lyophilization the Adam BDP acid conjugated terminal amine trimer 17 (32%) is obtained.

3. Radiochemistry

The BDP acid conjugated terminal amine monomer 14 and Adam BDP acid conjugated terminal amine trimer 17 are radiolabeled with [$^{99m}$Tc-MAS$_3$]-NHS, which is prepared with high radiochemical purity (>99%) and high specific activity in DMSO using a solid-phase pre-loading technique within 20 min {Misra, 2007}. In brief, for radiolabeling, dried BDP acid conjugated terminal amine monomer 14 and Adam BDP acid conjugated terminal amine trimer 17 are suspended in DMSO at a concentration of 25 µM. Conjugation is performed by the addition of 500 µL of [$^{99m}$Tc-MAS$_3$]-NHS (148 MBq or 4 mCi, 0.36 nmol) in 50 µL (12.5 µM) of the ligand in DMSO, followed by addition of 5 µL (20 µmol) triethylamine (4 M). Constant stirring at RT is maintained for 1 h. The radiolabeled [$^{99m}$Tc-MAS$_3$] BDP acid conjugated monomer 15a and [$^{99m}$Tc-MAS$_3$]Adam BDP acid conjugated trimer 18a are purified by use of an analytical reverse phase HPLC. The HPLC fractions containing the $^{99m}$Tc-labeled monomer 15a and $^{99m}$Tc-labeled trimer 18a are collected, and concentrated under a rotary evaporator (70-80% radiochemical yield). The radiolabeled molecules are reconstituted in phosphate buffered saline for in vitro experiments.

4. Synthesis of [Re-MAS$_3$]-Conjugates

Conjugation of synthesized compounds 14 & 17 with [Re-MAS$_3$]—NHS {Misra, 2007} is performed by the addition of 0.1 mL (10 mmol) of 100 mM triethylamine in DMSO to 0.1 mL (1 mmol) of a 10 mM solution of the ligand compounds in DMSO, followed by addition of 0.2 mL (2 mmol) of a 10 mM [Re-MAS$_3$]-NHS solution in DMSO. Constant stirring at RT is maintained for 2 h. The conjugates are purified by preparative HPLC. The collected fractions are lyophilized to obtain cold version of monomer 15b and trimer 18b.

5. In Vitro Cell-Binding Assay $\alpha_v\beta_6$-positive human colon carcinoma cell line HT-29 {Kemperman, 1997} and $\alpha_v\beta_6$-negative human hepatoma cell line Huh-7 {Sainz, 2012} are cultured at 37° C. under humidified 5% CO$_2$ in RPMI 1640 medium (Mediatech Cellgro, Herndon, Va.) supplemented with 10% fetal bovine serum (Gemini Bio-Products, Woodland, Calif.) and 5% penicillin/streptomycin (Cambrex Bioscience, Walkersville, Md.). HT-29 cells express high levels of $\alpha_v\beta_6$-integrin which largely mediates attachment of these cells to fibronectin {Kemperman, 1997}, while Huh-7 cells do not. For binding experiments, both cell lines are seeded onto 96-well filter plates (model MSHAS4510, Millipore, Bedford, Mass.) and are grown to 50% confluence (approximately 35,000 cells per well) over 48 h.

In vitro integrin $\alpha_v\beta_6$-binding affinities and specificities of monomer 15 and trimer 18 are assessed via displacement cell binding assays using $^{99m}$Tc-labeled versions as the tracers and Re-labeled versions as the test compounds. Experiments are performed on HT-29, and Huh-7 cells by a previously described method {Misra, 2007}.

REFERENCES

1. Breuss J M, Gallo J, DeLisser H M, et al. Expression of the beta 6 integrin subunit in development, neoplasia and tissue repair suggests a role in epithelial remodeling. *J. Cell Sci.* 1995, 108, 2241-2251.
2. Midwood K S, Mao Y, Hsia H C, Valenick L V, Schwarzbauer J E. Modulation of cell-fibronectin matrix interactions during tissue repair. *J. Investig. Dermatol. Symp. Proc.* 2006, 11, 73-78.
3. Munger J S, Huang X, Kawakatsu H, et al. The integrin alpha v beta 6 binds and activates latent TGF beta 1: a mechanism for regulating pulmonary inflammation and fibrosis. *Cell.* 1999, 96, 319-328.
4. Kessler H. Peptide conformations. Part 19. Conformation and biological effects of cyclic peptides. *Angew. Chemie.* 1982, 94, 509-520.
5. Kloczewiak M, Timmons S, Lukas T J, Hawiger J. Platelet receptor recognition site on human fibrinogen. Synthesis and structure-function relationship of peptides corresponding to the carboxy-terminal segment of the gamma chain. *Biochemistry* 1984, 23, 1767-1774.
6. Kraft S, Diefenbach B, Mehta R, Jonczyk A, Luckenbach G A, Goodman S L. Definition of an unexpected ligand recognition motif for alphav beta6 integrin. *J. Biol. Chem.* 1999, 274, 1979-1985.
7. Conti M, Bendriem B, Casey M, Chen M, Kehren F, Michel C, Panin V. First experimental results of time-of-flight reconstruction on an LSO PET scanner. *Phys. Med. Biol.* 2005, 50, 4507-4526.
8. Surd S, Karp J S, Popescu L M, Daube-Witherspoon M E, Werner M. Investigation of time-of-flight benefit for fully 3-D PET. *IEEE Trans Med. Imaging* 2006, 25, 529-538.
9. Kelloff G J, Hoffman J M, Johnson B, et al. Progress and promise of FDG-PET imaging for cancer patient management and oncologic drug development. *Clin. Cancer Res.* 2005, 11, 2785-2808.
10. Kumar R A, Chauhan H, Zhuang M, Chandra P, Schnall M, alavi A. Standardized uptake values of normal breast tissue with 2-deoxy-2[F-18]fluoro-D: -glucose positron emission tomography: variations with age, breast density, and menopausal status. *Mol. Imaging Biol.* 2006, 8, 355-362.
11. Kitov P I, Bundle D R. On the nature of the multivalency effect: a thermodynamic model. *J. Am. Chem. Soc.* 2003, 125, 16271-16284.
12. Mammen M, Chio S K, Whitesides G M. Polyvalent interactions in biological systems: implications for design and use of multivalent ligands and inhibitors. *Angew. Chem., Int. Ed.* 1998, 37, 2755-2794.
13. Lindhorst T K. Artificial multivalent sugar ligands to understand and manipulate carbohydrate-protein interactions. *Top. Curr. Chem.* 2002, 218, 201-235.
14. Lundquist J J, Toone E J. The cluster glycoside effect. *Chem. Rev.* 2002, 102, 555-578.
15. Wright D, Usher L. Multivalent binding in the design of bioactive compounds. *Curr. Org. Chem.* 2001, 5, 1107-1131.
16. Carlson C, Mowery P, Owen R, Dykhuizen E, Kiessling, L. Selective tumor cell targeting using low-affinity, multivalent interactions. *ACS Chem. Biol.* 2007, 2, 119-127.
17. Thumshirn G, Hersel U, Goodman S L, Kessler H. Multimeric cyclic RGD peptides as potential tools for tumor targeting: solid-phase peptide synthesis and chemoselective oxime ligation. *Chem. Eur. J.* 2003, 9, 2717-2725.
18. Voegtle F, Richardt G, Werner N. *Dendritische Molekule*; B. G. Teubner Verlag: Wiesbaden, Germany, 2007.
19. Haag R, Kratz F. Polymer therapeutics: concepts and applications. *Angew. Chem., Int. Ed.* 2006, 45, 1198-1215.
20. Friedman S L. Hepatic stellate cells: protean, multifunctional, and enigmatic cells of the liver. *Physiol Rev.* 2008, 88, 125-172.
21. Schuppan D, Afdhal N H. Liver cirrhosis. *Lancet* 2008, 371, 838-851.
22. Popov Y, Patsenker E, Stickel F, et. al. Integrin alphavbeta6 is a marker of the progression of biliary and portal liver fibrosis and a novel target for antifibrotic therapies. *J. Hepatol.* 2008, 48, 453-464.
23. Humblet V, Misra P, Bhushan K R, et al. Multivalent scaffolds for affinity maturation of small molecule cell surface binders and their application to prostate tumor targeting. *J. Med. Chem.* 2009, 52, 544-550.
24. Misra P, Humblet V, Pannier N, et. al. Production of multimeric prostate-specific membrane antigen small-molecule radiotracers using a solid-phase 99 mTc preloading strategy. *J Nucl Med.* 2007, 48, 1379-1389.
25. Kemperman H, Wijnands Y M, Roos E. alphaV Integrins on HT-29 colon carcinoma cells: adhesion to fibronectin is mediated solely by small amounts of alphaVbeta6, and alphaVbeta5 is codistributed with actin fibers. *Exp Cell Res.* 1997, 234, 156-164.
26. Sainz B, Barretto N, Yu X, Corcoran P, Uprichard SL. Permissiveness of human hepatoma cell lines for HCV infection. *Virology J.* 2012, 9, 30-39.

What is claimed is:

1. A method of making a contrast agent, said method comprising:

(a) providing an organic chelating ligand, wherein said organic chelating ligand selected from the group consisting of:

wherein

R is t-butyl ester, ester or hydrogen; and $R^1$ is (b) reacting said organic chelating ligand with a linking moiety, wherein said linking moiety having a primary amine and a carboxylic moiety at opposing ends;

(c) deprotecting one or more carboxylic acid ester of said organic chelating ligand to yield one or more carboxylic acid functionality;

(d) chelating a metal ion to result in a metal chelate, wherein said linking moiety on said metal chelate having said carboxylic moiety;

(e) providing a multivalent scaffold, wherein said multivalent scaffold is selected from the group consisting of:

-continued wherein
$R^2$ is Boc, Fmoc, Ac, Cbz, Bz or Bn;
$L_1$ and $L_2$ are linkers; and
$R^1$ is (f) conjugating said multivalent scaffold with a targeting ligand to yield one or more targeting ligand conjugated multivalent scaffold;
(g) deprotecting an amino protecting group on said one or more targeting ligand conjugated multivalent scaffold to obtain an amine containing targeting ligand conjugated multivalent scaffold; and
(h) reacting said amine containing targeting ligand conjugated multivalent scaffold with said carboxylic moiety of said metal chelate under a condition capable of forming an amide bond to results in said contrast agent.

2. The method of claim 1, wherein said linkers $L_1$ and $L_2$ are selected from the group consisting of alkane, amino acid, $—NHCO(CH_2)_5—$, polyethylene glycol and polypropylene glycol.

3. The method of claim 1, wherein said contrast agent is in a form of pharmaceutically acceptable salts, hydrates and solvates.

4. The method of claim 1, wherein said targeting ligand is wherein $L_3$ is independently selected from the group consisting of alkane, amino acid, polyethylene glycol and polypropylene glycol.

5. The method of claim 1, wherein said metal ion is selected from the group consisting of Cu, Tc Mn, Re, In, Tb, Tm, Tl, Sm, Lu, Ga, Yb, Y, Gd, Eu, and a lanthanide.

6. The method of claim 5, wherein Cu, Fe, Mn, Tm, Yb, Y, Gd, Eu, or a lanthanide is chelated for magnetic resonance imaging.

7. The method of claim 5, wherein Cu, Tc, Re, In, Tb, Tm, Tl, Sm, Lu, Ga, or Y is chelated for nuclear imaging.

8. A method of making a contrast agent, said method comprising:
(a) providing an organic chelating ligand, wherein said organic chelating ligand selected from the group consisting of wherein
R is t-butyl ester, ester or hydrogen; and
$R^1$ is (b) reacting said organic chelating ligand with a linking moiety to yield a terminal carboxylic moiety on said organic chelating ligand, wherein said linking moiety having a primary amine and a carboxylic moiety at opposing ends;

(c) providing a multivalent scaffold, wherein said multivalent scaffold is selected from the group consisting of wherein
R² is Boc, Fmoc, Ac, Cbz, Bz or Bn;
L₁ and L₂ are linkers; and
R¹ is (d) conjugating said multivalent scaffold with a targeting ligand to yield one or more targeting ligand conjugated multivalent scaffold;

(e) deprotecting an amino protecting group on said one or more targeting ligand conjugated multivalent scaffold to obtain an amine containing targeting ligand conjugated multivalent scaffold;

(f) reacting said amine containing targeting ligand conjugated multivalent scaffold with said terminal carboxylic moiety on said organic chelating ligand under a condition capable of forming an amide bond to results in an organic chelating ligand containing targeting ligand conjugated multivalent scaffold;

(g) deprotecting one or more carboxylic acid ester of said organic chelating ligand containing targeting ligand conjugated multivalent scaffold to yield one or more carboxylic acid functionality; and (h) chelating a metal ion to said one or more carboxylic acid functionality on said organic chelating ligand containing targeting ligand conjugated multivalent scaffold to results in said contrast agent.

9. The method of claim 8, wherein said linkers $L_1$ and $L_2$ are selected from the group consisting of alkane, amino acid, —NHCO(CH₂)₅—, polyethylene glycol and polypropylene glycol.

10. The method of claim 8, wherein said contrast agent is in a form of pharmaceutically acceptable salts, hydrates and solvates.

11. The method of claim 8, wherein said targeting ligand is wherein $L_3$ is independently selected from the group consisting of alkane, amino acid, polyethylene glycol and polypropylene glycol.

12. The method of claim 8, wherein said metal ion is selected from the group consisting of Cu, Tc, Fe, Mn, Re, In, Tb, Tm, Tl, Sm, Lu, Ga, Yb, Y, Gd, Eu, and a lanthanide.

13. The method of claim 12, wherein Cu, Fe, Mn, Tm, Yb, Y, Gd, Eu, or a lanthanide is chelated for magnetic resonance imaging.

14. The method of claim 12, wherein Cu, Tc, Re, In, Tb, Tm, Tl, Sm, Lu, Ga, or Y is chelated for nuclear imaging.

* * * * *